(12) United States Patent
Smith et al.

(10) Patent No.: US 9,534,990 B2
(45) Date of Patent: Jan. 3, 2017

(54) ARRANGEMENT FOR PRESERVATION OF BIOLOGICAL SAMPLES

(75) Inventors: Michael John Smith, Cardiff (GB); Stevan Paul Tortorella, Wells, ME (US)

(73) Assignee: GE Healthcare UK Limited, Little Chalfont (GB)

( * ) Notice: Subject to any disclaimer, the term of this patent is extended or adjusted under 35 U.S.C. 154(b) by 0 days.

(21) Appl. No.: 14/005,909

(22) PCT Filed: Mar. 15, 2012

(86) PCT No.: PCT/SE2012/050287
§ 371 (c)(1),
(2), (4) Date: Sep. 18, 2013

(87) PCT Pub. No.: WO2012/128702
PCT Pub. Date: Sep. 27, 2012

(65) Prior Publication Data
US 2014/0011289 A1    Jan. 9, 2014

(30) Foreign Application Priority Data
Mar. 18, 2011   (GB) .................. 1104607.5

(51) Int. Cl.
*G01N 1/00* (2006.01)
*G01N 1/31* (2006.01)
*B01L 7/00* (2006.01)
*G01N 1/28* (2006.01)
*G01N 1/44* (2006.01)
*B01L 3/00* (2006.01)
*G01N 1/40* (2006.01)

(52) U.S. Cl.
CPC ............... *G01N 1/312* (2013.01); *B01L 7/00* (2013.01); *G01N 1/2813* (2013.01); *G01N 1/44* (2013.01); *B01L 3/5029* (2013.01); *B01L 3/5055* (2013.01); *B01L 2200/0678* (2013.01); *B01L 2300/0822* (2013.01); *G01N 2001/2826* (2013.01); *G01N 2001/4027* (2013.01); *Y10T 436/2525* (2015.01)

(58) Field of Classification Search
CPC .................................................. G01N 1/312
USPC ............................... 436/169, 176; 422/551
See application file for complete search history.

(56) References Cited

U.S. PATENT DOCUMENTS 4,756,299 A    7/1988    Podella
5,980,828 A    11/1999    McClintock et al.
(Continued)

FOREIGN PATENT DOCUMENTS

EP    0570867    11/1993
JP    2-502519    8/1990
(Continued)

OTHER PUBLICATIONS

B. Sandnes, The physics and the chemistry of the heat pad, Am. J. Phys. 76 (6), Jun. 2008, pp. 546-550.*
(Continued)

*Primary Examiner* — Chrostopher A Hixson
*Assistant Examiner* — Emily Berkeley

(57) ABSTRACT

The present invention generally relates to systems and methods for preserving biological samples and, more particularly, an arrangement for drying biological samples disposed on sample storage substrates. The systems and methods for preserving biological samples can include a heating element such as a chemical heating pad that facilitates drying of the biological samples.

14 Claims, 9 Drawing Sheets

(56) References Cited

U.S. PATENT DOCUMENTS

| | | | |
|---|---|---|---|
| 7,748,283 B2 * | 7/2010 | Harvey et al. | ............. 73/864.91 |
| 8,062,901 B2 | 11/2011 | Dai et al. | |
| 8,468,901 B2 | 6/2013 | Harvey et al. | |
| 2002/0146696 A1 * | 10/2002 | Burgoyne et al. | ................. 435/6 |
| 2006/0204950 A1 * | 9/2006 | Ilercil et al. | ................... 435/1.1 |
| 2006/0246598 A1 * | 11/2006 | Dai | ...................... B01L 3/5023 |
| | | | 436/169 |
| 2007/0117173 A1 * | 5/2007 | Levison et al. | ................. 435/23 |
| 2008/0268495 A1 | 10/2008 | Skold et al. | |
| 2010/0221830 A1 * | 9/2010 | Sadler | .......................... 435/374 |
| 2011/0086380 A1 | 4/2011 | Skold et al. | |

FOREIGN PATENT DOCUMENTS

| | | | |
|---|---|---|---|
| JP | 03-189536 | 8/1991 | |
| JP | 05-261127 | 10/1993 | |
| JP | 3008328 | 3/1995 | |
| WO | 2009/009113 | 1/2009 | |
| WO | WO 2009/126099 | 10/2009 | |
| WO | WO 2009126099 A1 * | 10/2009 | ............... G01N 1/44 |

OTHER PUBLICATIONS

"Thermo-Pad: FAQ" accessed by the examiner at http://thermo-pad.com/faq.htm on Jul. 9, 2014.*

Stringer, M. Dennis, C.. (2000). Chilled Foods (2nd Edition). Woodhead Publishing.*

* cited by examiner

ARRANGEMENT FOR PRESERVATION OF BIOLOGICAL SAMPLES

CROSS-REFERENCE TO RELATED APPLICATIONS

This application is a filing under 35 U.S.C. 371 of international application number PCT/SE2012/050287, filed Mar. 15, 2012, published on Sep. 27, 2012 as WO 2012/128702, which claims priority to Great Britain patent application number 1104607.5 filed Mar. 18, 2011.

TECHNICAL FIELD OF THE INVENTION

The present invention relates to preservation of biological samples and more particularly to an arrangement for drying of biological samples on sample storage substrates. The invention also relates to a method of biological sample preservation on sample storage substrates.

BACKGROUND OF THE INVENTION

Paper substrates and similar porous sheet substrates are commonly used for preservation of biological samples. Examples are the chemically treated FTA® and FTA® Elute papers (GE Healthcare) for preservation of nucleic acid samples and the FTA® DMPK cards and 903® cards (GE Healthcare) for preservation of blood samples. A common feature for the methods of using these substrates is that a wet biological sample (blood, buccal swabs, macerated tissue etc.) is placed on the substrate, absorbed in the porous structure and dried. If the drying is incomplete or slow, the stability of the sample may be impaired and inconsistent results may be obtained in subsequent analyses of components in the preserved samples. The standard procedure is to dry the substrate with the sample in ambient air, which leads to long drying times—up to 18 h—before complete water removal, during which time degradation and mould or bacterial growth may cause deterioration of the sample.

Several devices for preservation of samples on paper substrates have been described, e.g. the buccal cell sampling device of U.S. Pat. No. 7,748,283. The drying of the sample on the substrate in such devices is done under ambient conditions, which can be slow—particularly if the humidity is high.

U.S. Pat. No. 6,703,216 mentions that chemical heat pads can be used to evaporate interfering ethanol in gammahydroxybutyrate dipstick analyses, but this publication does not relate to preservation of biological samples and does not describe any drying of such samples.

Accordingly there is a need for a method and a device that provides improved stability and consistency in preservation of biological samples on porous sheet substrates.

SUMMARY OF THE INVENTION

One aspect of the invention is to provide rapid and consistent drying of biological samples on porous sheet substrates. This is achieved with an arrangement for drying of a biological sample applied on a sample storage substrate, comprising at least one sample storage substrate holder and at least one chemical heat pad. One advantage of this arrangement is that rapid and consistent drying can be obtained in the field without access to electricity or any laboratory appliances.

A further aspect of the invention is to provide high recoveries of analytes from dried biological samples on porous sheet substrates. This is achieved with a method for preservation of at least one biological sample comprising the steps of:
a) providing at least one sample storage substrate;
b) applying the biological sample on the sample storage substrate;
c) positioning at least one chemical heat pad in proximity of the sample storage substrate;
d) activating the chemical heat pad to accelerate the drying of the biological sample; and
e) storing the sample storage substrate with the dried biological sample for at least 24 h.

One advantage is that high recoveries of proteins and nucleic acids can be obtained even under difficult ambient conditions.

Further suitable embodiments of the invention are described herein.

DEFINITIONS

Figure 1:
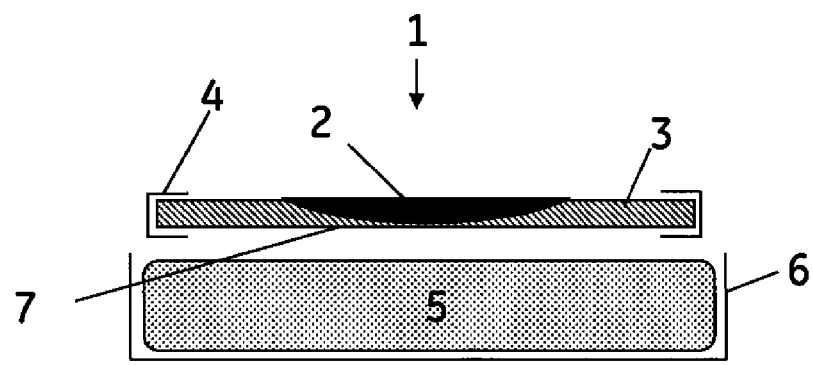
FIG. 1 shows an arrangement according to the invention.
Figure 2:
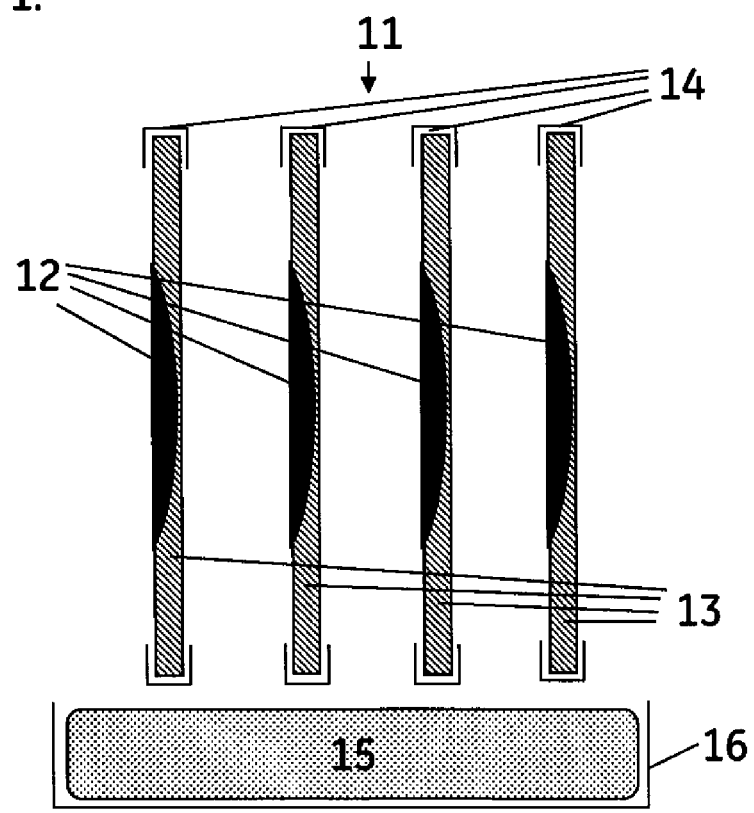
FIG. 2 shows an alternative arrangement according to the invention.
Figure 3:
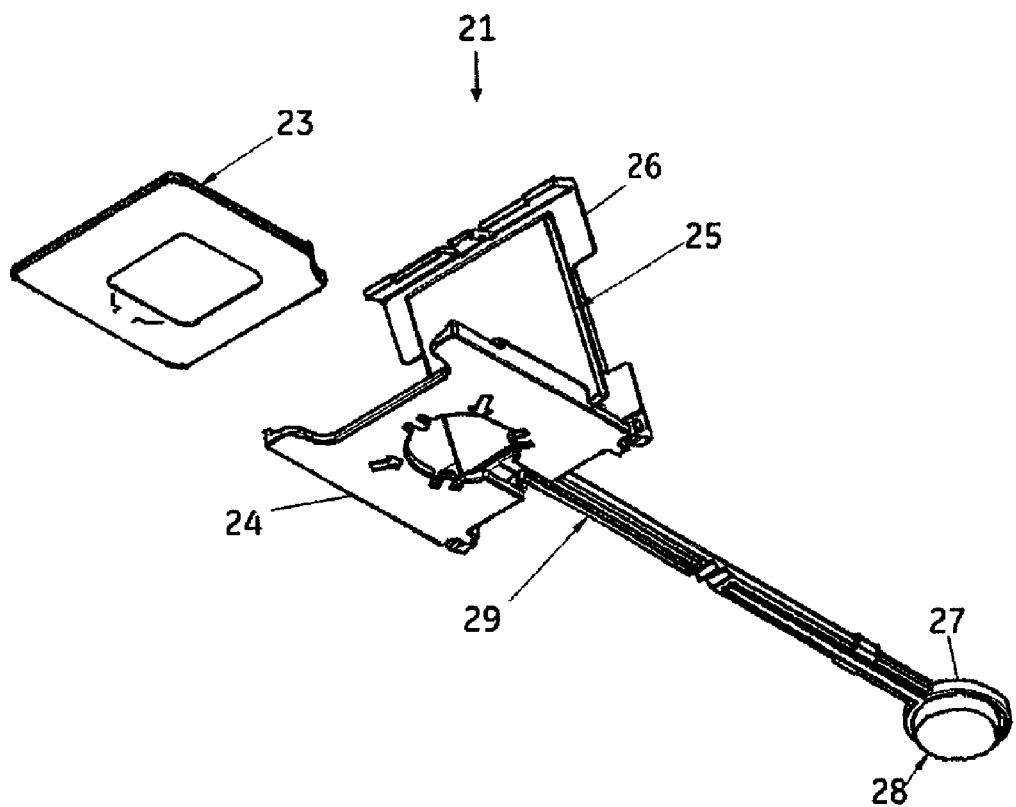
FIG. 3 shows an arrangement according to the invention.
Figure 4:
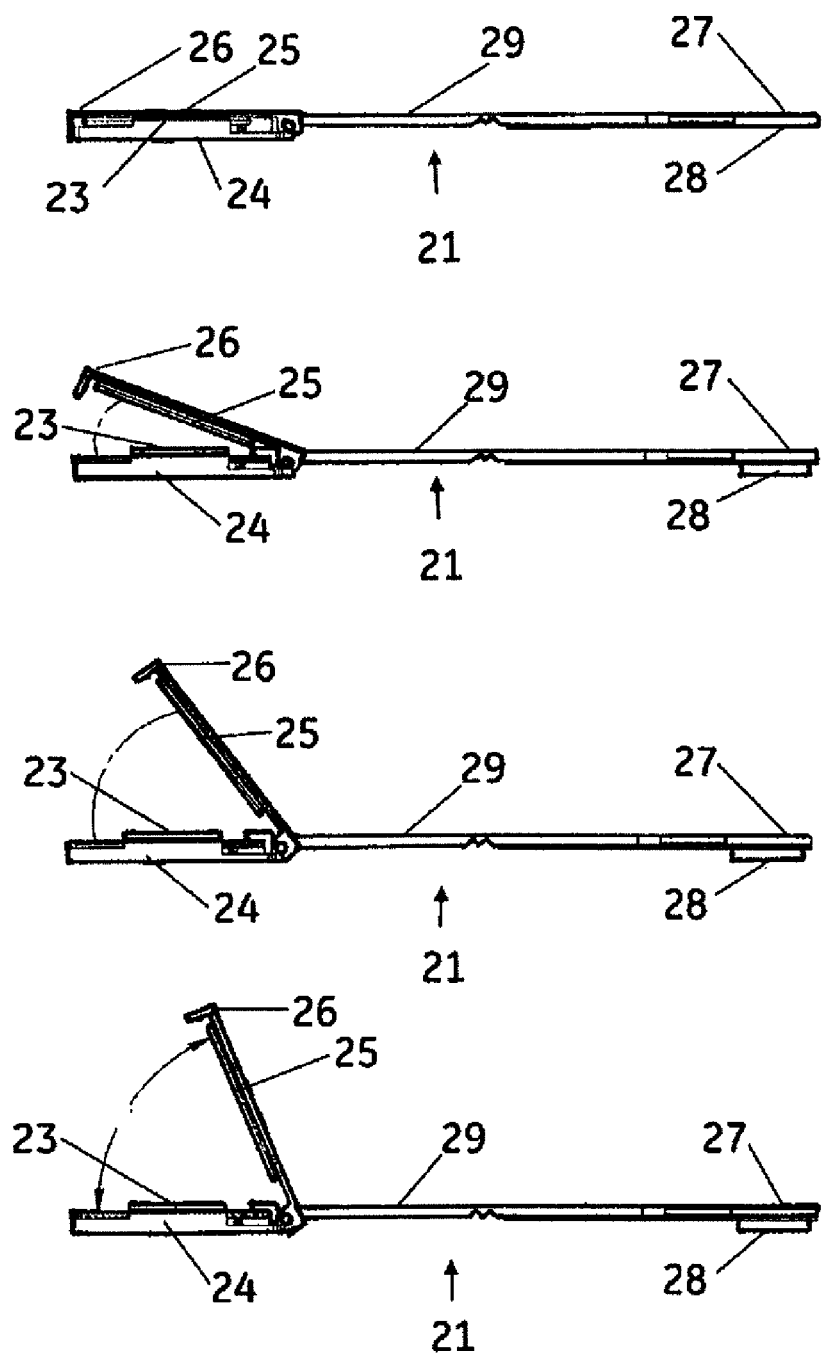
FIG. 4 shows side views of the arrangement in FIG. 3 with a hinged chemical heat pad holder at different angles of the hinge.
Figure 5:
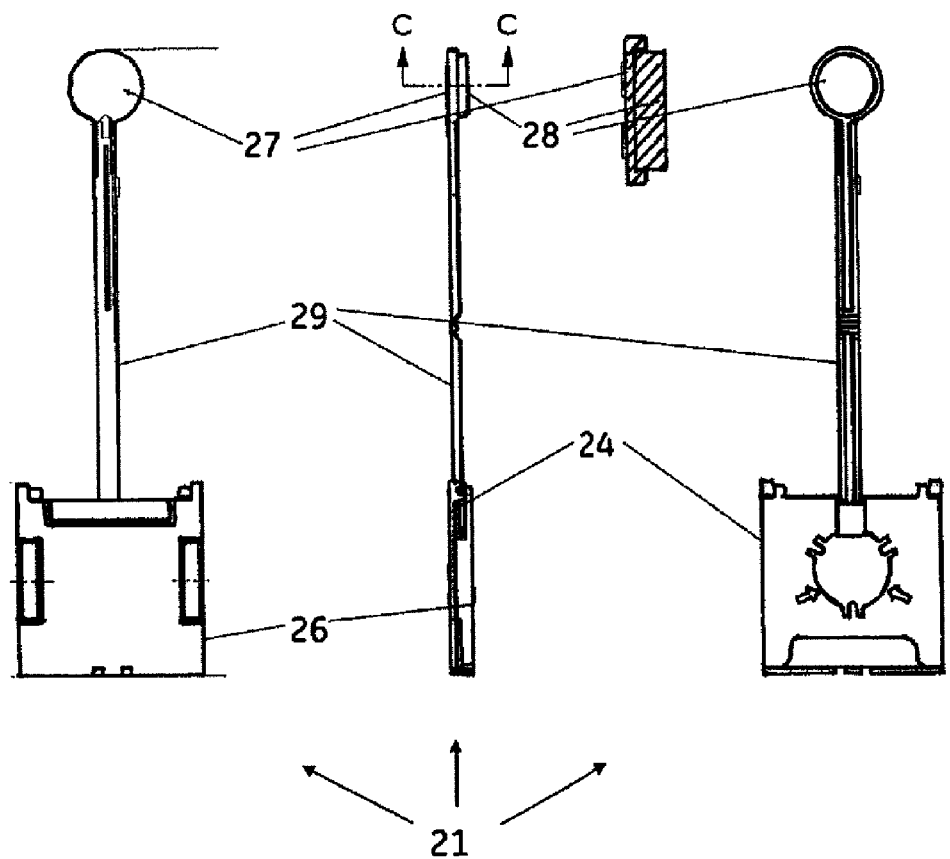
FIG. 5 shows top and side views of the arrangement in FIGS. 3 and 4.
Figure 6:
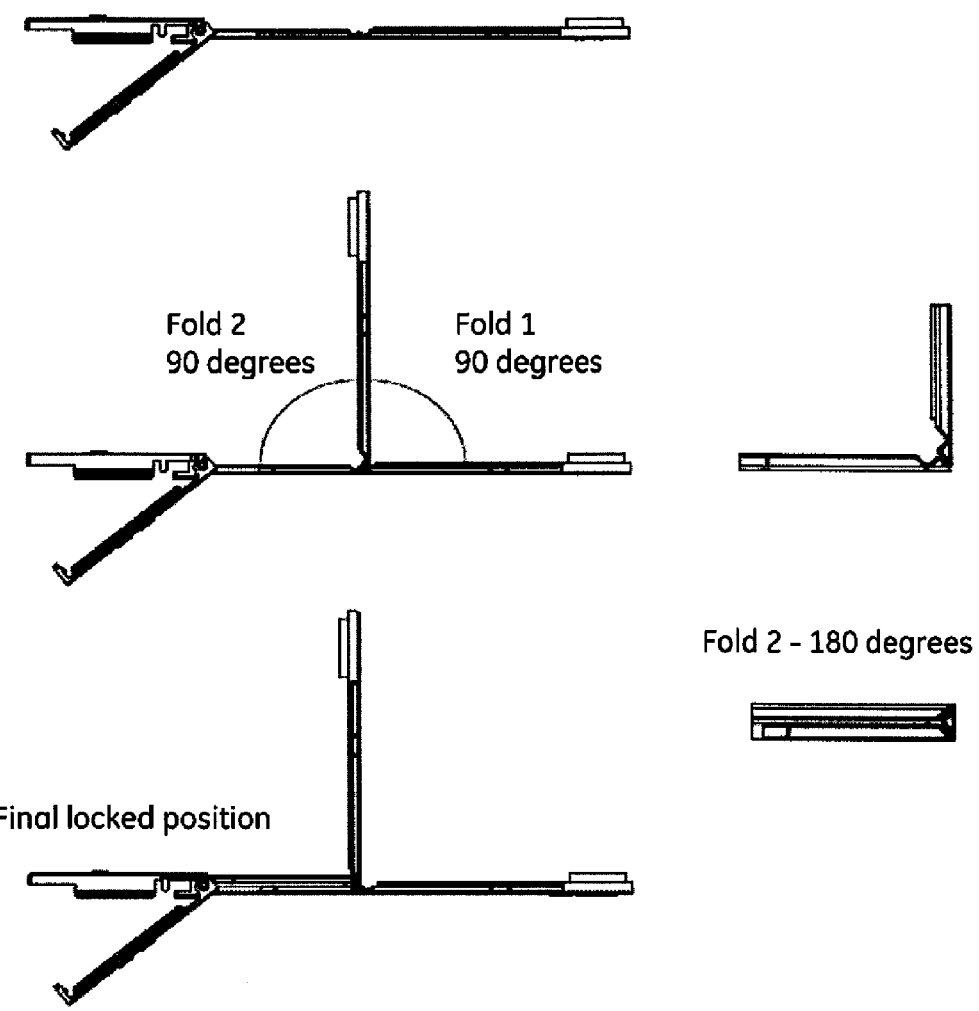
FIG. 6 shows the arrangement of FIGS. 3-5 with a moveable sample collection member in different positions.

The term "paper" as used herein means a fibrous web or sheet material. Paper comprises fibres, e.g. cellulose or glass fibres, and optionally other components, such as e.g. particulate fillers, wet strength or dry strength additives, retention agents etc. It can also comprise reagents for preservation of sample components, lysis of cells etc.

DETAILED DESCRIPTION OF EMBODIMENTS

In one aspect illustrated by FIGS. 1-9, the present invention discloses an arrangement for drying of a biological sample 2 applied on a sample storage substrate 3;13;23;33, comprising at least one sample storage substrate holder 4;14;24;34 and at least one chemical heat pad 5;15;25;35. In other words, the arrangement comprises at least one holder for a sample storage substrate and at least one chemical heat pad, which may optionally be placed in a chemical heat pad holder 6;16;26;36. The arrangement may optionally be a device comprising a sample storage substrate holder, a chemical heat pad holder and at least one chemical heat pad. The chemical heat pad is either in proximity of the sample substrate or is arranged so that it can be moved into proximity of the sample storage substrate. Upon activation of the chemical heat pad, heat will transfer to the sample storage substrate and cause a gentle drying of the sample on the substrate.

An advantage of the arrangement is that it allows rapid drying of the sample, even under difficult ambient conditions, which allows for improved recoveries of sample components and improved robustness of analytical methods.

Chemical heat pads are available in several different varieties. They contain chemical reagents that upon activation start an exothermic phase transition, chemical or electrochemical reaction. One common category is chemical heat pads comprising supersaturated salt solutions. When the pad is activated e.g. by bending a slit metal disk or a metal spring inside the solution, crystallisation of the salt is started and heat is generated as long as the (exothermic) crystallisation reaction is ongoing. The maximum temperature reached inside the crystallising solution is self-regulated by the melting temperature of the crystals formed and the rate of crystallisation (which affects the heat flow and the duration of the heating) can be controlled by formulation of the salt solution, e.g. by adding viscosity-increasing additives to slow down the rate. The surface temperature of the pad is controlled by the crystallisation but also by the thermal conductivity of the pad material, the dimensions of the pad and by the rate of heat loss from the pad. A commonly used material in supersaturated salt solution heat pads is sodium acetate trihydrate with a melting point of about 58° C., but other materials with different melting points are available and it is also possible to manipulate the melting temperature of sodium acetate by the addition of other materials. An advantage of supersaturated salt solution heat pads is that they are reusable, i.e. they can after use be heated above the melting temperature, cooled and activated again. They are also easy to activate by bending the slit disk/spring, which provides a possibility to integrate an activation means into the drying arrangement (heat pads requiring mixing of solutions or reagents are not amenable to these particular arrangements). Examples of commercially available sodium acetate trihydrate heat pads include EZHeat and The Heat Solution (both Pristech Products Inc, USA), Repeat Heat (Repeat Heat Factory Ltd, China) and Therma-Pak (PASS Bracing, Canada)

It is also possible to use chemical heat pads where the heat is generated by the reaction between reagents that are brought into contact with each other upon activation. One example is heat pads containing iron powder and a salt solution, which are activated by providing access to atmospheric oxygen to start oxidation of the iron. Such heat packs can be made smaller but are not reusable and have a less well defined maximum temperature. Examples of commercially available iron powder heat pads include Hand Warmer and Adhesive Body Warmer Plaster (both Evergreen Medical & Hygienic Products Co Ltd, China).

In some embodiments the sample storage substrate 3;13; 23;33 comprises a sheet of porous material, such as paper. Paper is a convenient material with suitable absorption properties and mechanical properties, but it is also possible to use other porous materials such as e.g. polymeric foams or membranes. The sample storage substrate may have a thickness less than 1 mm, such as 0.3-0.7 mm and it may be in a card format, either self-supported or encased in a frame. It may further comprise printed or embossed indications of the sample application area and it may comprise an identifying code e.g. in the form of a number, bar code, RFID tag etc.

In certain embodiments the sample storage substrate 3;13;23;33 comprises at least one reagent for stabilization of components in the biological sample or for lysis of cells in the sample. Chemical reagents may increase the stability of certain inherently unstable components, e.g. nucleic acids, where complexing agents and/or radical scavengers etc. may be used as stabilisers and proteins, where e.g. polyhydric compounds such as sugars or polyvinyl alcohol can have stabilising effects. Lysis of cells can be accomplished with e.g. surfactants or chaotropes and is desirable e.g. in the preservation and analysis of nucleic acids. Suitable stabilising reagents are described in e.g. U.S. Pat. No. 5,496,562 (nucleic acids) and EP 1,423,514 A2 (proteins). Reagents for lysis of cells can e.g. be surfactants, in particular anionic surfactants like e.g. sodium dodecyl sulphate (SDS), or chaotropes like guanidinium salts or urea. Stabilizing reagents can be e.g. chelating agents (e.g. EDTA), weak bases (e.g. Tris or bis-Tris), radical traps (e.g. uric acid or urate salts) and/or vitrification-promoting polyhydroxy compounds (e.g. dextran, polysucrose, trehalose etc). All of these reagents make the paper more hygroscopic.

In some embodiments the ceiling surface temperature of the chemical heat pad 5;15;25;35 is about 60° C. or lower, such as between 35 and 58° C. The ceiling surface temperature is the maximum temperature reached by the surface of the chemical heat pad after activation and an advantage of avoiding high ceiling temperatures is that if the sample comprises heat-sensitive components, the risk for overheating these is diminished. The surface temperature can be measured by placing a chemical heat pad on a bench top at room temperature, placing a thermometric transducer on the top of the heat pad, activating the heat pad and recording the temperature.

In certain embodiments the chemical heat pad 5;15;25;35 is capable of maintaining a surface temperature within the 35-58° C. interval during at least 10 min, such as at least 60 min. A short drying time (e.g. 10 min) may be sufficient when the heat pad is placed in contact with the sample storage substrate, while longer times (up to 1 h) may be needed when the heat pad is placed adjacent to a plurality of sample storage substrates. The size and character of the chemical heat pad can be selected to provide suitable duration of the heating.

In some embodiments the chemical heat pad 5;15;25;35 is positioned at a distance of less than about 10 mm, such as less than about 2 mm from the sample storage substrate 3;13;23;33. A short distance provides for efficient heat transfer and drying.

In certain embodiments the chemical heat pad 5;15;25;35 is positioned in contact with the sample storage substrate 3;13;23;33. The heat pad can if so desired be positioned in contact with the back side 7 of the sample storage substrate to diminish the risk of sample contamination. It is also possible to position a protective film (not shown) between the heat pad and the sample storage substrate to further diminish the contamination risk. In this case the heat pad will be in indirect contact with the sample storage substrate via the protective film.

In some embodiments, illustrated by FIGS. 3-7, the chemical heat pad 25 is placed in a chemical heat pad holder 26 which is hinged and moveable towards the sample storage substrate 23. An advantage of this is that the heat pad can conveniently be activated and immediately placed in contact with or at a close distance from the sample storage substrate.

Figure 7:
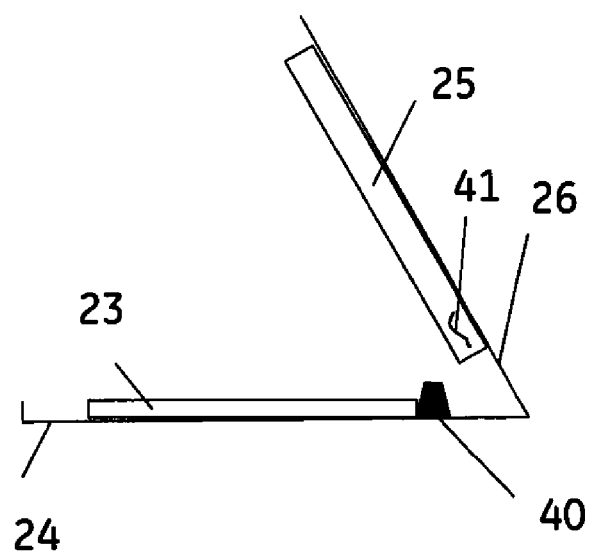
FIG. 7 shows an arrangement with a hinged chemical heat pad holder and activation means at different angles of the hinge.
Figure 7:
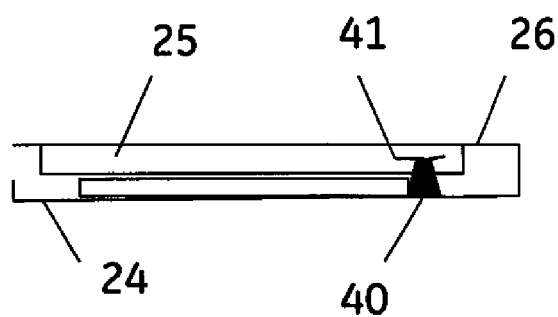

In certain embodiments illustrated by FIG. 7, the arrangement also comprises an activating means 40, capable of activating the chemical heat pad 25. The activating means can e.g. be a protrusion on or adjacent to the sample storage substrate holder 24 or the movable sample collection member 27, that causes a slit metal disk or spring 41 in the heat pad to bend upon positioning of the heat pad or upon moving the sample collection member to a closed position. The slit metal disk or spring may in this case be located at a specific position in the heat pad, e.g. in a partly sealed-off corner of the pad, to fit with the protrusion during positioning. In other words, the activation means (protrusion) can be arranged to act on a slit metal disk or a spring located inside the heat pad upon contacting the activation means (protrusion) with the heat pad. Advantages of having an activating means in the arrangement include that the activation is facilitated, that the heat pad does not need to be touched and that the time between activation and positioning of the heat pad can be shortened.

In some embodiments illustrated by FIGS. 3-6, the arrangement also comprises a moveable sample collection member 27 with an analyte collection surface 28. This moveable sample collection member can be hinged and capable to move between a first open position for collecting the biological sample on the analyte collection surface and a second closed position facing or contacting at least a portion of the sample storage substrate. The moveable sample collection member can e.g. be attached to a hinged arm 29. Such an arrangement can be useful in e.g. the sampling of buccal epithelial cells in human identification, where the sample collection member in the open position can be entered through the mouth and the analyte collection surface swabbed against the inside of the cheek to collect cells. The sample collection member can then be closed and the analyte collection surface brought into contact with the sample storage substrate to transfer the cells. Then the chemical heat pad can be positioned and activated to accelerate the drying of the cell sample. The analyte collection surface 28 can e.g. be a polymer foam and the sample storage substrate can e.g. be a paper card treated with cell lysing and/or nucleic acid (e.g. DNA) or protein preserving reagents, e.g. FTA®, FTA DMPK or FTAElute (GE Healthcare).

Figure 8:
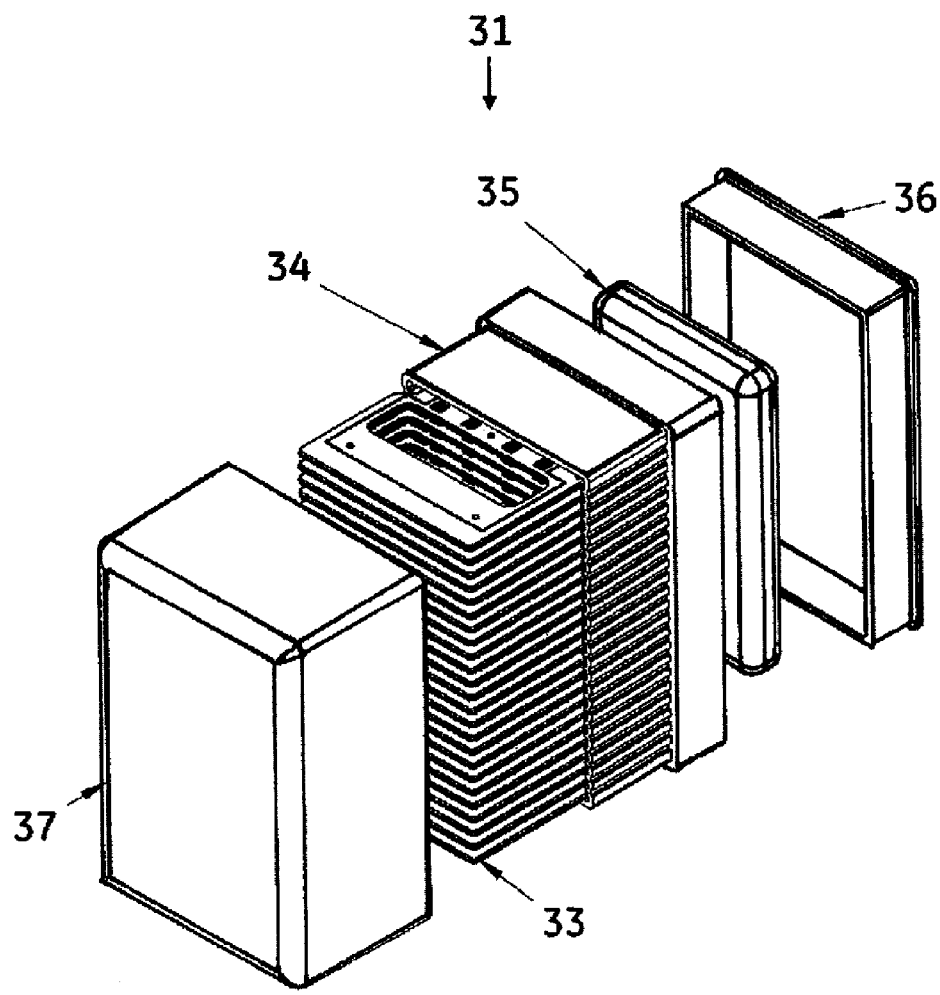
FIG. 8 shows an arrangement according to the invention.
Figure 9:
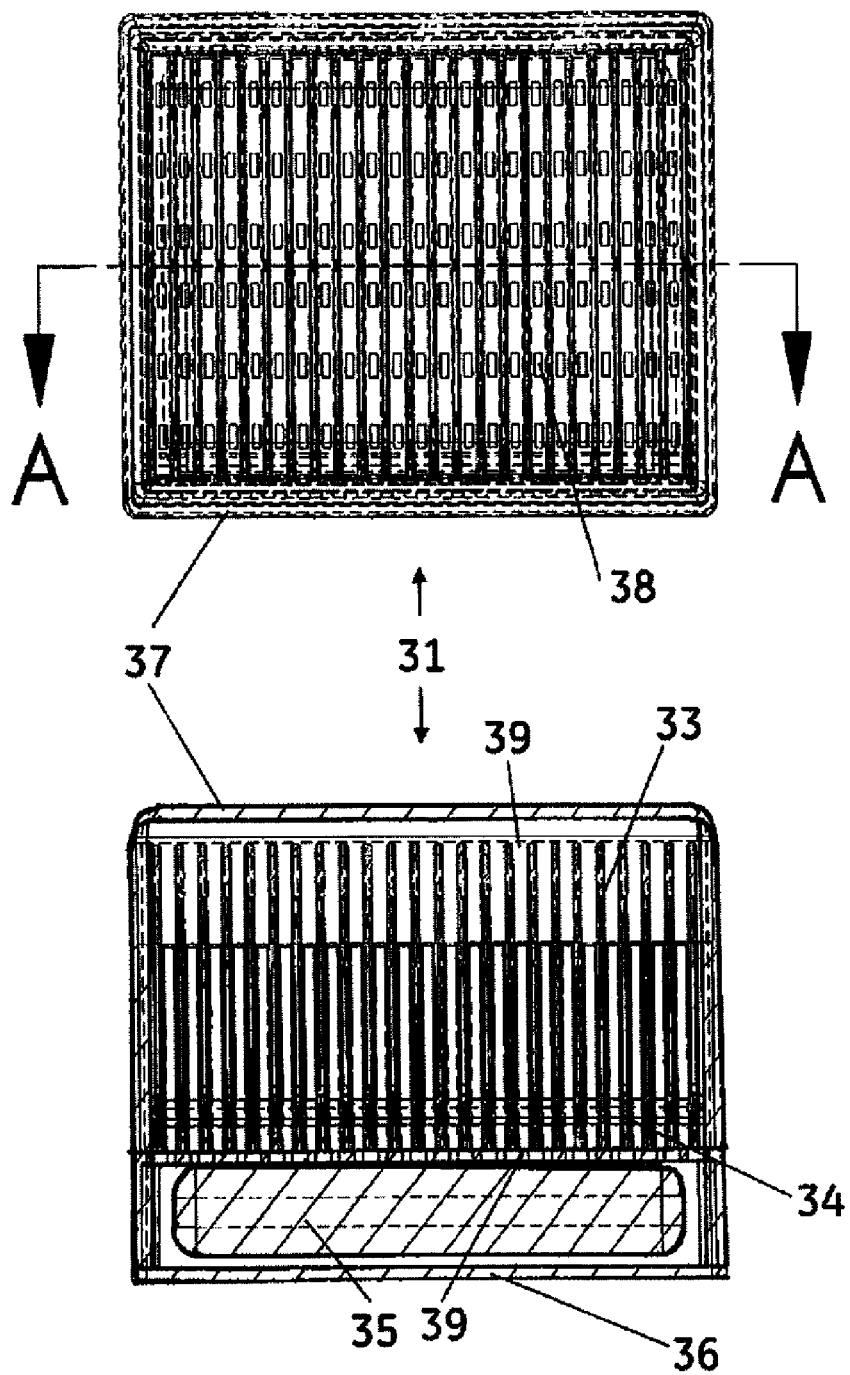
FIG. 9 shows top and side views of the arrangement in FIG. 7.
Figure 10:
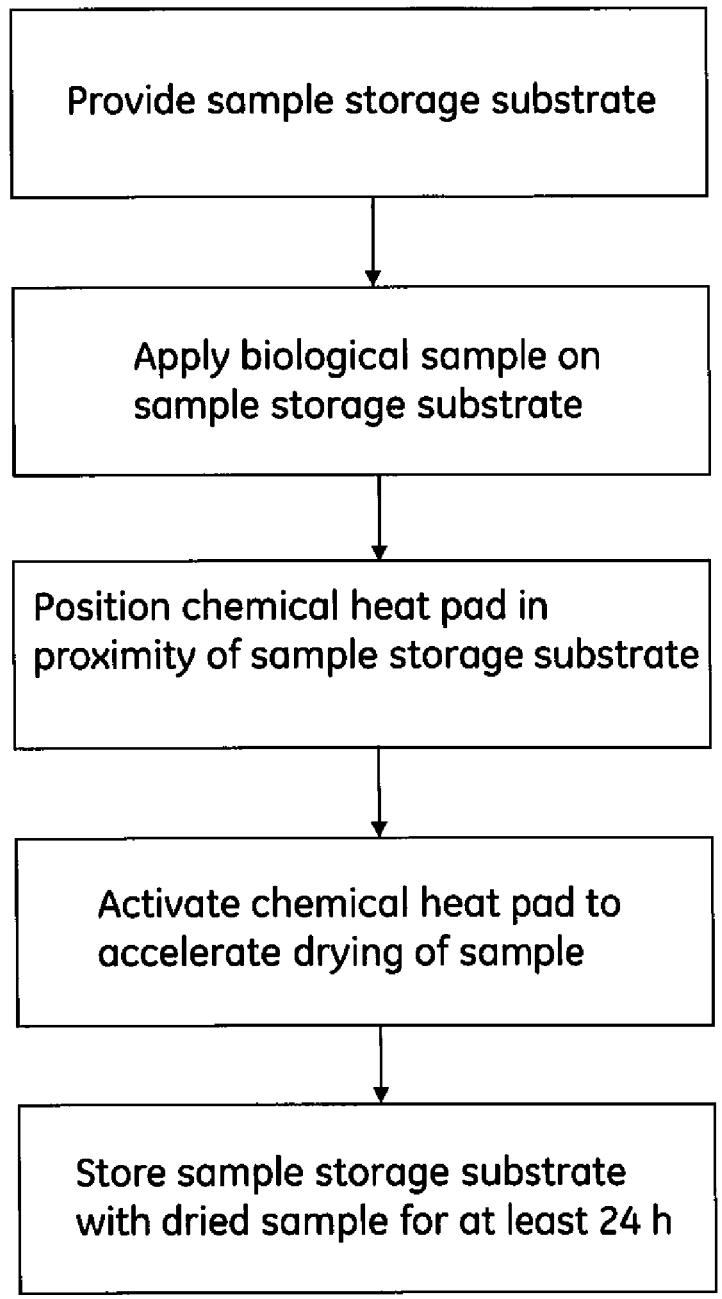
FIG. 10 shows a method according to the invention.

In certain embodiments, illustrated by FIGS. 8-9, the arrangement comprises a housing 37 with a plurality of sample storage substrates 33. The housing may comprise air vents 38 in connection with air channels 39 between the sample storage substrates. An advantage of this arrangement is that several samples may be applied to different substrates and rapidly dried in one operation. The air vents 38 on the housing can be aligned with the air channels 39 to obtain an efficient convective heat transfer from the heat pad 35. The heat pad can be positioned below the sample storage substrates 33 to improve the convection and the sample storage substrates can be positioned perpendicular or inclined to the length axis of the heat pad. The sample storage substrate holder 34 can be a magazine capable of receiving at least 10, such as 24, sample storage substrates, e.g. in the format of plastic framed paper cards. The sample storage substrates can be used to sample blood from animals or humans during e.g. drug metabolism and pharmacokinetics (DMPK) testing of drug candidates. In this case, the entire magazine may be transported to a central analysis facility for analysis of the dried blood spots.

In one aspect, illustrated by FIGS. 1-10, the invention discloses a method for preservation of at least one biological sample. The method comprises the steps of a) providing at least one sample storage substrate 3;13; 23;33, b) applying the biological sample on the sample storage substrate, c) positioning at least one chemical heat pad 5;15;25;35 in proximity of the sample storage substrate, d) activating the chemical heat pad to accelerate the drying of the biological sample and e) storing the sample storage substrate with the dried biological sample for at least 24 h. An advantage of this method is that rapid and reproducible drying of the sample can be achieved, even under difficult ambient conditions, leading to better sample recoveries and improved robustness. The method can e.g. be performed using the arrangements described in previous embodiments. Features of the method embodiments described below are also applicable to the arrangement embodiments described above.

In some embodiments the surface of the chemical heat pad after activation reaches a temperature in the interval 35-58° C. and maintains a temperature in this interval for at least 10 min, such as at least 60 min. This can be achieved e.g. with commercially available sodium acetate trihydrate heat pads of different constructions. An advantage is that overheating of any heat-sensitive sample components can be avoided and that rapid drying can be achieved.

In certain embodiments the moisture content of the biological sample or the sample storage substrate with the biological sample is less than about 25% by weight or less than about 15% by weight within one hour after step d), such as within 10 min after step d). An advantage of this is that degradation of components in the sample is prevented.

In some embodiments the sample storage substrate 3;13; 23;33 comprises a sheet of porous material, such as paper. Examples of such substrates are non-modified papers such as 903® or 31ETF (both GE Healthcare) and papers with lysing/preservation reagents such as FTA, FTA DMPK and FTAElute (all GE Healthcare). Papers comprising lysing or preservation reagents are often more hygroscopic than plain papers and the method and arrangement of the invention can be particularly advantageous when such papers are used.

In certain embodiments the sample storage substrate 3;13;23;33 comprises at least one reagent for stabilization of components in said biological sample or for lysis of cells in said sample. Examples of such substrates are FTA, FTA DMPK and FTAElute (all GE Healthcare). Reagents for lysis of cells can e.g. be surfactants, in particular anionic surfactants like e.g. sodium dodecyl sulphate (SDS), or chaotropes like guanidinium salts or urea. Stabilizing reagents can be e.g. chelating agents (e.g. EDTA), weak bases (e.g. Tris or bis-Tris), radical traps (e.g. uric acid or urate salts) and/or vitrification-promoting polyhydroxy compounds (e.g. dextran, polysucrose, trehalose etc). All of these reagents make the paper more hygroscopic.

In some embodiments the method also comprises a step f) of analyzing at least one component in said sample, after step e). The analysis may involve e.g. mass spectrometric analysis of drug candidates or their metabolites, immunoassays of proteins or PCR/RT-PCR and detection of specific nucleic acid sequences.

EXAMPLES

Example 1

Surface Temperature Study

Two sodium acetate trihydrate pads (diameter 90 mm, weight 100 g) were evaluated in duplicate, after reheating and cooling. Each pad was placed on a benchtop at room temperature (20+/−2° C.) with a temperature transducer (Comark C28 K type thermocouple) on top of it and after activation the temperature was logged.

Results:

| Time (min) | Orange pad Series 1 (° C.) | Orange pad Series 2 (° C.) | Blue pad Series 1 (° C.) | Blue pad Series 2 (° C.) |
|---|---|---|---|---|
| 0 | 44.8 | 45.0 | 41.0 | 44.0 |
| 5 | 48.1 | 47.8 | 43.9 | 46.0 |
| 10 | 47.8 | 47.6 | 42.0 | 45.2 |
| 15 | 47.4 | 46.8 | 41.2 | 45.4 |
| 20 | 46.8 | 46.3 | 40.4 | 44.4 |
| 25 | 46.2 | 46.1 | 40.2 | 44.3 |
| 30 | 45.7 | 45.7 | 39.0 | 43.4 |
| 35 | 45.1 | 44.9 | 39.2 | 42.6 |
| 40 | 44.5 | 44.0 | 38.8 | 42.3 |
| 45 | 42.6 | 41.8 | 37.9 | 41.5 |
| 50 | 42.0 | 42.4 | 37.3 | 40.1 |
| 55 | 41.6 | 41.3 | 37.0 | 39.6 |
| 60 | 40.6 | 40.8 | 34.5 | 38.4 |
| Max | 48.1 | 47.8 | 43.9 | 46.0 |
| Min | 40.6 | 40.8 | 34.5 | 38.4 |
| Mean | 44.89 | 44.65 | 39.42 | 42.86 |

The results show that both pads were able to maintain a surface temperature within the 41-48° C. interval for 10 min and within the 35-48° C. interval for 60 min.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An arrangement for drying of a biological sample applied on a sample storage substrate, comprising:
at least one sample storage substrate comprising a front side for receiving the biological sample and a back side, the sample storage substrate being formed of a paper material;
at least one sample storage substrate holder;
at least one chemical heat pad positioned below the back side of the sample storage substrate;
a chemical heat pad holder that is hinged and moveable towards the sample storage substrate so as to position the chemical heat pad in proximity of the sample storage substrate; and
a protrusion, wherein said protrusion is configured to activate said chemical heat pad to accelerate the drying of the biological sample on the sample storage substrate,
wherein a ceiling surface temperature of said chemical heat pad is between 35 and 58° C., and
wherein the sample storage substrate holder comprises one or more air passageways, the one or more air passageways being arranged to expose the sample storage substrate to air outside the sample storage substrate holder when the sample storage substrate holder is in a closed configuration.

2. The arrangement of claim 1, wherein said sample storage substrate comprises a sheet of porous material.

3. The arrangement of claim 1, wherein said sample storage substrate further comprises at least one reagent for stabilization of components in said biological sample or for lysis of cells in said sample.

4. The arrangement of claim 1, wherein said chemical heat pad is configured to maintain a surface temperature within the 35-58° C. interval for at least 10 min.

5. The arrangement of claim 1, wherein the chemical heat pad is positioned at a distance of less than about 10 mm from said sample storage substrate.

6. The arrangement of claim 1, wherein the chemical heat pad is positioned in contact with said sample storage substrate.

7. The arrangement of claim 1, wherein said protrusion is arranged to act upon a slit metal disk or spring in said chemical heat pad.

8. The arrangement of claim 1, further comprising a moveable sample collection member hinged and configured to move between a first open position for collecting the biological sample on the analyte collection surface and a second closed position facing or contacting at least a portion of the sample storage substrate, wherein said sample collection member has an analyte collection surface.

9. The arrangement of claim 1, further comprising a housing with a plurality of said sample storage substrates and wherein said housing comprises air vents in connection with air channels between the sample storage substrates.

10. The arrangement of claim 1, wherein said sample storage substrate comprises at least one reagent for lysis of cells in said sample.

11. The arrangement of claim 1, wherein said sample storage substrate comprises a surfactant or a chaotrope.

12. The arrangement of claim 1, wherein said sample storage substrate comprises an anionic surfactant, a guanidinium salt or urea.

13. The arrangement of claim 1, wherein the sample storage substrate is positioned perpendicularly to a length axis of the heat pad.

14. The arrangement of claim 1, further comprising a protective film between the chemical heat pad and the sample storage substrate.

* * * * *